United States Patent [19]

Jadesjö et al.

[11] Patent Number: 5,474,938
[45] Date of Patent: Dec. 12, 1995

[54] METHOD OF ANALYSIS HYDROGEN PEROXIDE

[75] Inventors: Gunilla Jadesjö, Kungälv; Bertil Magnusson, Göteborg; Signar Sundstrand, Stenungsund, all of Sweden

[73] Assignee: Eka Nobel AB, Bohus, Sweden

[21] Appl. No.: 180,816

[22] Filed: Jan. 10, 1994

Related U.S. Application Data

[63] Continuation of Ser. No. 786,607, Nov. 1, 1991, abandoned.

[30] Foreign Application Priority Data

Nov. 2, 1990 [SE] Sweden ................................ 9003496

[51] Int. Cl.$^6$ .......................... G01N 33/00; G01N 33/18
[52] U.S. Cl. ....................... 436/135; 436/164; 436/166; 436/174; 436/176; 422/63; 422/68.1; 422/82.05; 422/82.09
[58] Field of Search ......................... 436/71, 76, 135, 436/166, 164, 176, 805, 905, 174; 422/82.05, 82.09, 62, 68.1

[56] References Cited

U.S. PATENT DOCUMENTS

| | | | |
|---|---|---|---|
| 3,595,755 | 7/1971 | Härtel | 436/135 |
| 3,898,042 | 8/1975 | Webb et al. | 23/230 R |
| 4,143,080 | 3/1979 | Harders et al. | 23/230 B |
| 4,186,251 | 1/1980 | Tarbutton | 431/11 |
| 4,587,100 | 5/1986 | Amano et al. | 422/56 |
| 4,680,271 | 7/1987 | Williams | 436/55 |
| 4,900,682 | 2/1990 | Fischer et al. | 436/129 |
| 4,908,323 | 3/1990 | Werner | 436/135 |
| 4,933,277 | 6/1990 | Abe et al. | 435/28 |
| 5,004,696 | 4/1991 | Clinkenbear | 436/51 |

FOREIGN PATENT DOCUMENTS 0418798  3/1991  European Pat. Off. .

OTHER PUBLICATIONS

John C. Kutt, "Rapid Determination of Trace Peroxide", Aseptipac I, Conference in Princeton, NJ (1984).
H. Lux, "Praktikum der quantitativen anorganischen Analyse", pp. 117–119, 1970.
Analytical Abstracts Database, Royal Society of Chemistry, Cambridge, GB, M. A. Abdalla et al, "Flow–Injection Amperometric Determination of Hydrogen Peroxide at Low Level in Aqueous Solution", Accession No. 52-05-B-00007.
Analytical Abstracts Database, Royal Society of Chemistry, Cambridge, GB, A. Chamsi et al, "Application of the Reductive Flow≧Injection Amperometric Determination of Iodine . . . ", Accession No. 49-05-B-00152.

*Primary Examiner*—James C. Housel
*Assistant Examiner*—Long V. Le
*Attorney, Agent, or Firm*—Burns, Doane, Swecker & Mathis

[57] ABSTRACT

The invention relates to a method of determining the content of hydrogen peroxide in an aqueous solution, which is brought to a pH below 3, supplied with an excess of I$^-$, and irradiated with light, the absorbance being measured at a predetermined wavelength. The invention also relates to an analyser for carrying out the method. Further, the invention relates to a method and a system of controlling the supply of hydrogen peroxide to an aqueous solution.

8 Claims, 1 Drawing Sheet

METHOD OF ANALYSIS HYDROGEN PEROXIDE

This application is a continuation of application Ser. No. 07/786,607, filed Nov. 1, 1991, now abandoned.

The invention relates to a method of determining the intent of hydrogen peroxide in an aqueous solution, which is brought to a pH below 6, supplied with an excess of I$^-$, and irradiated with light, the absorbance being measured at a predetermined wavelength. The invention also relates to an analyser for carrying out the method. Further, the invention relates to a method and a system of controlling the supply of hydrogen peroxide to an aqueous solution.

Hydrogen peroxide has wide commercial use, for instance for bleaching, disinfection and cleaning. To avoid unnecessary excess or deficiency of hydrogen peroxide, it is desirable to have simple and reliable methods of analysis. Content determinations are largely performed manually, e.g. by iodometric titration. A common method consists in acidifying the solution, adding potassium iodide in excess, adding ammonium molybdate as catalyst, as well as an indicator, e.g. Thyodene solution, and finally titrating with sodium thiosulphate until all iodine formed has been converted back to iodide. This and other manual methods are time-consuming and little adapted for use in many modern processes where it is desirable to have an automatically controlled addition of hydrogen peroxide.

J. C. Kutt, "Rapid Determination of Trace Peroxide", Aseptipac I, Conference in Princeton, N.J., 1984, describes an automatic method of analysis based on the same principles as the manual methods, that is acidification of the sample and addition of iodide and molybdate. The iodine excess is thereafter determined amperometrically. This method is satisfactory at low hydrogen peroxide contents, but is not recommended for high contents. Moreover, it requires relatively complicated and thus expensive equipment.

U.S. Pat. No. 4,143,080 describes another method of analysis based on similar principles. The pH of the sample is set within a range of 6.0 to 7.5, and the iodine excess is determined photometrically. This method is comparatively slow and is therefore not suitable for automatic systems controlling supply of hydrogen peroxide.

There is thus a need for a simple and reliable method of determining the content of hydrogen peroxide in aqueous solutions. This method should permit being automated and connected to a control system for automatic supply of hydrogen peroxide.

It has now been found that the above-mentioned need can be satisfied by the present invention. This relates to a method of determining the content of hydrogen peroxide in an aqueous solution, as stated in the claims.

The invention is based on the known reaction:

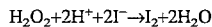

$$H_2O_2 + 2H^+ + 2I^- \rightarrow I_2 + 2H_2O$$

If iodide is supplied in excess, the amount of iodine formed in the aqueous solution is substantially proportional to the amount of hydrogen peroxide in the original sample. According to the present invention, a sample solution is brought to a pH below 6 and supplied with iodide in excess, resulting in rapid formation of iodine. The sample solution is then irradiated with light, and the absorbance is measured at a predetermined wavelength which is so selected that the light is absorbed, at least partly, by iodine in the aqueous solution, the absorbance value obtained being a measure of the hydrogen peroxide content of the original sample.

The method of analysis according to the invention can be used at temperatures ranging from 0° to 100° C. in most environments as long as no interfering substances are present. Examples of substances which should be avoided are oxidation agents which, like hydrogen peroxide, oxidise iodide into iodine, such as Cr(VI)-compounds or permanganate. Also, substances consuming iodine should be avoided, such as unsaturated organic substances, which may add iodine to the double bonds.

A suitable amount of I$^-$ may be from about 1.5 to about 3 mole per mole $H_2O_2$ in the sample solution, and it is preferably added in the form of alkali metal iodide, e.g. potassium iodide or sodium iodide. It is however obvious to those skilled in the art that other iodides may be used as well. Since the reaction requires an excess of H$^+$, the analysis is suitably carried out at a pH ranging from 1 to 6, preferably from 3 to 6. In order to bring the sample solution to a suitable pH, the addition of an acid is often required. The acid could be inorganic or organic, but should not in itself be an interfering substance. Examples of usable acids are sulphuric acid, hydrochloric acid and acetic acid.

In order to further increase the speed of the reaction where iodine is set free, a catalyst is suitably added to the solution. For example, a catalysing amount of molybdate, preferably ammonium molybdate or metal molybdate such as alkali metal molybdate, most preferably ammonium molybdate, is then added. A suitable amount of molybdate may be from about 1 mmole to about 10 mmole per mole $H_2O_2$ in the sample solution.

The absorbance is suitably measured by measuring the amount of light of a predetermined wavelength which passes upon irradiation through the sample solution before and after addition of the reagents, i.e. iodide and optionally acid and catalyst. If P designates the amount of radiation energy of a certain wavelength which passes through the sample after the addition of all the reagents, and $P_0$ designates the amount of radiation energy of the same wavelength which passes through a similar sample, but without the addition of any reagents, the absorbance is equal to the logarithm of the quotient $P_0/P$. This quotient is approximately proportional to the content of iodine in the solution, which in turn, according to the above reaction formula, is essentially proportional to the hydrogen peroxide content of the original sample. A calibration curve relating to the exact relationship between the hydrogen peroxide content and the absorbance at a certain wavelength can easily be determined by those skilled in the art.

Irradiation is suitably carried out with essentially monochromatic light of such a wavelength that it is absorbed, at least partly, by iodine in the aqueous solution. Suitable wavelengths can easily be determined by a man skilled in the art. For instance, light having a wavelength of 530 nm has been found to serve its purpose excellently.

The method according to the invention can be used within a wide concentration range of hydrogen peroxide and is particularly suitable at concentrations from about 0.1 to about 500 mg/l, preferably from about 30 to about 150 mg/l. At higher contents, there is a risk of precipitation of iodine, which can however be avoided if the sample is diluted prior to analysis. If the content is too low, the speed of reaction is too slow for practical use of the method.

Thanks to the high speed of reaction, the method according to the invention can easily be automated and controlled, e.g. by means of a microcomputer. According to a preferred embodiment, sampling, addition of reagents and absorbance measurement are performed automatically and may be controlled by a computer. Suitably, the computer also performs all calculations. Preferably, sampling and analysis are carried out continuously at predetermined time intervals, e.g. from about 3 times per minute to every tenth minute.

A specific embodiment of the invention relates to a method of automatically controlling the supply of hydrogen peroxide to an aqueous solution, the supply being based on the content of hydrogen peroxide in the aqueous solution, said content being automatically determined by the above described method of analysis. For example, the same computer may control the performance of the analysis and a dosing pump for supplying hydrogen peroxide to the aqueous solution. By the method, it is, for example, possible to maintain a certain content of hydrogen peroxide in the aqueous solution.

The invention also relates to an analyser for carrying out the described method of analysis. The analyser comprises a sample vessel, a light source for irradiating the sample with preferably monochromatic light, means for measuring the amount of light of a predetermined wavelength which passes upon irradiation through the sample, means for supplying and withdrawing samples, and means for converting absorbance into hydrogen peroxide content. Suitably, it also comprises a computer for controlling all functions and for carrying out all calculations.

Further, the invention relates to a system for automatically controlling the addition of hydrogen peroxide to an aqueous solution according to the above described method, the system comprising an analyser as described above. A preferred system further comprise a dosing pump and a computer for automatically controlling all the functions, preferably also including the functions of the analyser.

BRIEF DESCRIPTION OF THE DRAWING

One embodiment of the invention will now be described with reference to FIG. 1 schematically showing a diagram of a system for maintaining a certain content of hydrogen peroxide in an aqueous solution. The invention is however not restricted thereto, but many different embodiments are conceivable within the scope of the accompanying claims.

DETAILED DESCRIPTION OF THE PREFERRED EMBODIMENTS

Figure 1:
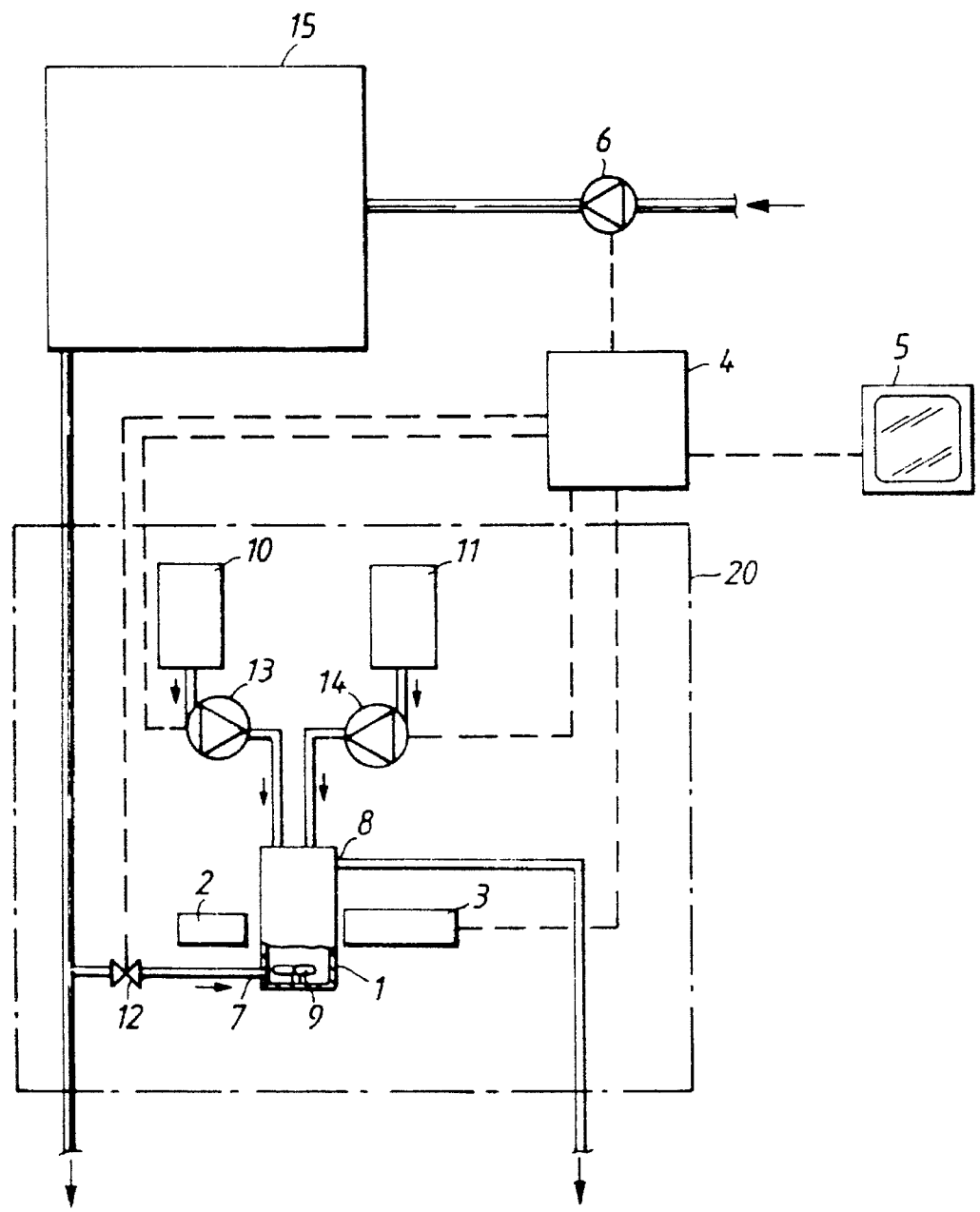

As shown in FIG. 1, the system comprises a hydrogen peroxide containing solution 15, e.g. a swimming pool, a dosing pump 6 connected to it for supplying hydrogen peroxide, an analyser 20 according to the invention, and a microcomputer 4 for controlling the system. For greater clarity, the analyser 20 and the microcomputer 4 are shown separated from each other, but in practice it is preferred that they are mounted in the same unit. The analyser 20 includes a sample cuvette 1 provided with an agitator 9 and having an inlet 7, equipped with a regulating valve 12, for supplying samples from the hydrogen peroxide containing solution 15, as well as an overflow 8 which is so positioned that a suitable sample quantity, e.g. about 2 ml, can be held in the cuvette 1. A light source 2 for monochromatic light having a wavelength of 530 nm is arranged to transmit light through the sample in the cuvette 1 towards a photocell 3 connected to the microcomputer 4. A tank 10 for potassium iodide solution is connected to the sample cuvette 1 over a dosing pump 13. Another tank 11 for a solution of ammonium molybdate and sulphuric acid is connected to the sample cuvette 1 over a dosing pump 14. The microcomputer 4 controls all the dosing pumps for reagents 13, 14 and hydrogen peroxide 6, as well as the regulating valve 12. A display 5 for manual reading is also connected to the microcomputer 4. It is however obvious to a man skilled in the art that the display is not necessary for the operation of the control system. It is also obvious that an analyser as described above can be used without being connected to a control system or that the operation of the control system itself is controlled by a separate, electronic or electromechanical unit which only receives the value of the hydrogen peroxide content from the analyser.

The system described above operates as follows. Hydrogen peroxide containing solution flows continuously through the inlet 7 into the sample cuvette 1 and out through the overflow 8. At predetermined time intervals, e.g. every second minute, the regulating valve 12 is closed, a suitable sample quantity remaining in the sample cuvette 1. This sample quantity is thereafter irradiated by the light source 2, and the amount of light passing through the sample is measured with the photocell 3, and the value is stored in the microcomputer 4. The dosing pumps 13, 14 for potassium iodide, sulphuric acid and ammonium molybdate are then activated. These substances are thus supplied to the sample in the cuvette 1, for instance in amounts from about 1 to about 50 μl. The sample solution is again irradiated, and the amount of transmitted light is measured by the photocell 3, stored in the microcomputer 4 and compared with the amount of light having passed through the sample without reagent. The quotient thereof is compared with a desired value, the dosing pump 6 being actuated, when desired, to replace hydrogen peroxide used in the aqueous solution 15. Also, the above-mentioned quotient is converted, on the basis of a calibration curve stored in the microcomputer, into hydrogen peroxide content shown in clear on the display 5. After completed measurement, the regulating valve 12 is opened and solution again flows through the cuvette until a new measurement is carried out.

We claim:

1. A method of determining a content of hydrogen peroxide in an aqueous solution, comprising the steps of (a) bringing a sample of the solution to a pH below 3, (b) adding iodide reagent in excess to the sample, (c) thereafter irradiating the sample with light, and (d) measuring the light absorbance and obtaining a value therefore at a predetermined wavelength which is so selected that the light is absorbed, at least partly, by iodine formed in the sample by reaction of the iodide with hydrogen peroxide, the absorbance value obtained being a measure of the hydrogen peroxide content of the sample prior to addition of iodide thereto.

2. A method as claimed in claim 1, wherein a catalyst reagent comprising ammonium molybdate or metal molybdate is added to the sample solution.

3. A method as claimed in claim 1, wherein the sample solution is supplied with an acid reagent comprising sulfuric acid, hydrochloric acid or acetic acid.

4. A method as claimed in claim 1, wherein the light absorbance measuring step includes passing light of a predetermined wavelength through the sample, and measuring the amount of light absorbed in the sample both before and after addition of any reagents to the sample.

5. A method as claimed in claim 2, wherein the light absorbance measuring step includes passing light of a predetermined wavelength through the sample, and measuring the amount of light absorbed in the sample both before and after addition of any reagents to the sample.

6. A method as claimed in claim 3, wherein the light absorbance measuring step includes passing light of a predetermined wavelength through the sample, and measuring the amount of light absorbed in the sample both before and after addition of any reagents to the sample.

7. A method as claimed in claim 1, including the step of automatically obtaining said sample from the solution, and wherein the steps of reagent addition and absorbance measurement are performed automatically.

8. A method of automatically controlling a supply of hydrogen peroxide supplied to an aqueous solution, the supply being based on a content of hydrogen peroxide in the aqueous solution, said content being automatically determined by a method comprising the steps of (a) bringing a sample of the solution to a pH below 3, (b) adding iodide reagent in excess to the sample, (c) thereafter irradiating the sample with light, (d) measuring the light absorbance and obtaining a value therefore at a predetermined wavelength which is so selected that the light is absorbed, at least partly, by iodine formed in the sample by reaction of the iodide with hydrogen peroxide, the absorbance value obtained being a measure of the hydrogen peroxide content of the sample prior to addition of iodide thereto, and (e) automatically supplying an amount of hydrogen peroxide based on said measurement of hydrogen peroxide content of the sample.

* * * * *